US010053743B2

(12) United States Patent
Yu et al.

(10) Patent No.: US 10,053,743 B2
(45) Date of Patent: Aug. 21, 2018

(54) METHOD FOR PREDICTING TREATMENT EFFICACY OF PEGINTERFERON PLUS RIBAVIRIN TREATMENT IN A SUBJECT SUFFERING FROM HEPATITIS C

(71) Applicant: KAOHSIUNG MEDICAL UNIVERSITY, Kaohsiung (TW)

(72) Inventors: Ming-Lung Yu, Kaohsiung (TW); Wan-Long Chuang, Kaohsiung (TW); Chia-Yen Dai, Kaohsiung (TW); Jee-Fu Huang, Kaohsiung (TW); Ming-Ying Lu, Magong (TW); Edward Hsi, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 41 days.

(21) Appl. No.: 15/367,111

(22) Filed: Dec. 1, 2016

(65) Prior Publication Data
US 2018/0148800 A1 May 31, 2018

(30) Foreign Application Priority Data

Nov. 25, 2016 (TW) .............................. 105138879 A

(51) Int. Cl.
*A61K 45/06* (2006.01)
*A61K 38/21* (2006.01)
*A61K 38/00* (2006.01)
*A61K 31/70* (2006.01)
*A61K 31/7056* (2006.01)
*C12Q 1/70* (2006.01)

(52) U.S. Cl.
CPC ....... *C12Q 1/707* (2013.01); *C12Q 2600/106* (2013.01); *C12Q 2600/158* (2013.01)

(58) Field of Classification Search
CPC .... A61K 31/506; A61K 31/519; A61K 31/52; A61K 31/5377; A61K 2800/782
See application file for complete search history.

(56) References Cited

PUBLICATIONS

Taylor et al., "Cyclic changes in gene expression induced by Peg-interferon alfa-2b plus ribavirin in peripheral blood monocytes (PBMC) of hepatitis C patients during the first 10 weeks of treatment", Journal of Translational Medicine, 2008, 6(66):1-15.*
Fried MW, Shiffman ML, Reddy KR, Smith C, Marinas G, Goncales FL, Jr., Haussinger D, Diago M, Carosi G, Dhumeaux D, Craxi A, Lin A, et al. Peginterferon alfa-2a plus ribavirin for chronic hepatitis C virus infection. N Engl J Med. 2002; 347:975-982.
Moreno C, Deltenre P, Pawlotsky JM, Henrion J, Adler M, Mathurin P. Shortened treatment duration in treatment-naive jenotype 1 HCV patients with rapid virological response: a meta-analysis. J Hepatol. 2010; 52:25-31.
Ge D, Fellay J, Thompson AJ, Simon JS, Shianna KV, Urban TJ, Heinzen EL, Qiu P, Bertelsen AH, Muir AJ, Sulkowski M, McHutchison JG, Goldstein DB. Genetic variation in IL28B predicts hepatitis C treatment-induced viral clearance.3. Nature. 2009; 461:399-401.
Ferenci P, Fried MW, Shiffman ML, Smith CI, Marinas G, Goncales FL, Jr., Haussinger D, Diago M, Carosi G, Dhumeaux D, Craxi A, Chaneac M, et al. Predicting sustained virological responses in chronic hepatitis C patients treated with peginterferon alfa-2a (40 KD)/ ribavirin. J Hepatol. 2005; 43:425-433.
Di Lello FA, Culasso AC, Parodi C, Bare P, Campos RH, Garcia G. New evidence of replication of hepatitis C virus in short-term peripheral blood mononuclear cell cultures. Virus Res. 2014; 191:1-9.
Vermehren J, Yu ML, Monto A, Yao JD, Anderson C, Bertuzis R, Schneider G, Sarrazin C. Multi-center evaluation of the Abbott RealTime HCV assay for monitoring patients undergoing antiviral therapy for chronic hepatitis C. J Clin Virol. 2011; 52:133-137.
Okamoto H, Tokita H, Sakamoto M, Horikita M, Kojima M, Iizuka H, Mishiro S. Characterization of the genomic sequence of type V (or 3a) hepatitis C virus isolates and PCR primers for specific detection. J Gen Virol. 1993; 74:2385-2390.
Tanaka Y, Nishida N, Sugiyama M, Kurosaki M, Matsuura K, Sakamoto N, Nakagawa M, Korenaga M, Hino K, Hige S, Ito Y, Mita E, Tanaka E, et al. Genome-wide association of IL28B with response to pegylated interferon-alpha and ribavirin therapy for chronic hepatitis C. Nat Genet. 2009; 41:1105-1109.
Irizarry RA, Hobbs B, Collin F, Beazer-Barclay YD, Antonellis KJ, Scherf U, Speed TP. Exploration, normalization, and summaries of high density oligonucleotide array probe level data. Biostatistics. 2003; 4:249-264.
Benjamini Y, Hochberg Y. Controlling the false discovery rate: a practical and powerful approach to multiple testing. Journal of the Royal Statistical Society, Series B. 1995; 57:289-300.
Hanley JA, McNeil BJ. A method of comparing the areas under receiver operating characteristic curves derived from the same cases. Radiology. 1983; 148:839-843.
Yu ML, Dai CY, Huang JF, Chiu CF, Yang YH, Hou NJ, Lee LP, Hsieh MY, Lin ZY, Chen SC, Hsieh MY, Wang LY, Chang WY, et al. Rapid virological response and treatment duration for chronic hepatitis C genotype 1 patients: a randomized trial. Hepatology. 2008; 47:1884-1893.

(Continued)

*Primary Examiner* — Barry A Chestnut
(74) *Attorney, Agent, or Firm* — Hannah M. Tien

(57) ABSTRACT

The present invention provides a method for predicting treatment efficacy of peginterferon plus ribavirin treatment in a subject suffering from chronic hepatitis C comprising: (a) measuring gene expression levels of genes comprising RSAD2, LOC26010, HERC5, HERC6, IFI44, SERPING1, IFITM3 and DDX60 of a blood sample from the subject after one week of the peginterferon plus ribavirin treatment; and (b) calculating a gene score according to cumulative fold change of the gene expression levels, when the gene score is equal to or higher than a cut-off value, the method predicts successful treatment of chronic hepatitis C with the peginterferon plus ribavirin treatment for the subject.

5 Claims, 4 Drawing Sheets
(2 of 4 Drawing Sheet(s) Filed in Color)

(56) References Cited

PUBLICATIONS

Lu My, Huang CI, Hsieh MY, Hsieh TJ, Hsi E, Tsai PC, Tsai YS, Lin CC, Hsieh MH, Liang PC, Lin YH, Hou NJ, Yeh ML, Huang CF, Lin ZY, Chen SC, Huang JF, Chuang WL, Dai CY, Yu ML. Dynamics of PBMC gene expression in hepatitis C virus genotype 1-infected patients during combined peginterferon/ribavirin therapy. Oncotarget. Aug. 17, 2016.

Ming-Ying Lu, Ching-I Huang, Ming-Yen Hsieh, Tusty-Juan Hsieh, Edward Hsi, Pei-Chien Tsai, Yi-Shan Tsai, Ching-Chih Lin, Meng-Hsuan Hsieh, Po-Cheng Liang, Yi-Hung Lin, Nai-Jen Hou, Ming-Lun Yeh, Chung-Feng Huang, Zu-Yau Lin; Shinn-Cherng Chen, Jee-Fu Huang, Wan-Long Chuang, Chia-Yen Dai, Ming-Lung Yu. Dynamics of PBMC gene expression in the hepatitis C virus genotype 1-infected patients during combined peginterferon/ribavirin therapy. 2016 APASL HCV Kaohsiung.

* cited by examiner

METHOD FOR PREDICTING TREATMENT EFFICACY OF PEGINTERFERON PLUS RIBAVIRIN TREATMENT IN A SUBJECT SUFFERING FROM HEPATITIS C

CROSS-REFERENCES TO RELATED APPLICATIONS

The present application claims priority to Taiwan Patent Application No. 105138879 filed on Nov. 25, 2016, incorporated herein by reference in its entirety.

FIELD OF THE INVENTION

The present invention is related to a method for predicting treatment efficacy of peginterferon plus ribavirin treatment in a subject suffering from hepatitis C.

BACKGROUND OF THE INVENTION

Hepatitis C virus (HCV) affects 180 million people worldwide and is the major cause of liver cirrhosis. Approximately 1%-4% of cirrhotic patients may progress to the development of hepatocellular carcinoma. There are six HCV genotypes and more than 50 subtypes worldwide. The most common HCV genotypes in Taiwan are genotypes 1b, 2a, 2b and 3a. Combined peginterferon (pegIFN) plus ribavirin therapy results in a suboptimal sustained virologic response (SVR) and intolerable adverse effects. Administration of a 48-week pegIFN/ribavirin regimen can achieve a SVR rate of 40%-70% in HCV genotype 1 infected patients. In contrast, the SVR rate is approximately 90% for HCV-2 or HCV-3 infected patients treated with pegIFN/ribavirin therapy for 24 weeks. New generation direct acting antiviral agents (DAAs) have fewer side effects and substantially improve the SVR rates up to 90% for HCV genotype 1. However, the high cost of DAAs limits their clinical application. Thus, the pegIFN/ribavirin regimen remains a mainstay of HCV therapy in developing countries.

Many viral and host factors are responsible for the pathogenesis of HCV infection. HCV genotypes (Fried M W, Shiffman M L, Reddy K R, Smith C, Marinos G, Goncales F L, Jr., Haussinger D, Diago M, Carosi G, Dhumeaux D, Craxi A, Lin A, et al. Peginterferon alfa-2a plus ribavirin for chronic hepatitis C virus infection. N Engl J Med. 2002; 347:975-982), viral loads (Moreno C, Deltenre P, Pawlotsky J M, Henrion J, Adler M, Mathurin P. Shortened treatment duration in treatment-naive genotype 1 HCV patients with rapid virological response: a meta-analysis. J Hepatol. 2010; 52:25-31), IL-28B polymorphisms (Ge D, Fellay J, Thompson A J, Simon J S, Shianna K V, Urban T J, Heinzen E L, Qiu P, Bertelsen A H, Muir A J, Sulkowski M, McHutchison J G, Goldstein D B. Genetic variation in IL28B predicts hepatitis C treatment-induced viral clearance. Nature. 2009; 461:399-401), and a rapid virologic response (RVR) (Ferenci P, Fried M W, Shiffman M L, Smith C I, Marinos G, Goncales F L, Jr., Haussinger D, Diago M, Carosi G, Dhumeaux D, Craxi A, Chaneac M, et al. Predicting sustained virological responses in chronic hepatitis C patients treated with peginterferon alfa-2a (40 K D)/ribavirin. J Hepatol. 2005; 43:425-433) have been proposed as important predictors for the treatment outcome of peginterferon plus ribavirin therapy. However, the reason why a substantial proportion of patients fail peginterferon plus ribavirin therapy remains unclear. Although HCV primarily replicates in hepatocytes, there is evidence that peripheral blood mononuclear cells (PBMCs) can serve as a suitable site for HCV extrahepatic replication (Di Lello F A, Culasso A C, Parodi C, Bare P, Campos R H, Garcia G. New evidence of replication of hepatitis C virus in short-term peripheral blood mononuclear cell cultures. Virus Res. 2014; 191:1-9). PBMCs are also potent producers of interferon to defend against virus invasion.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
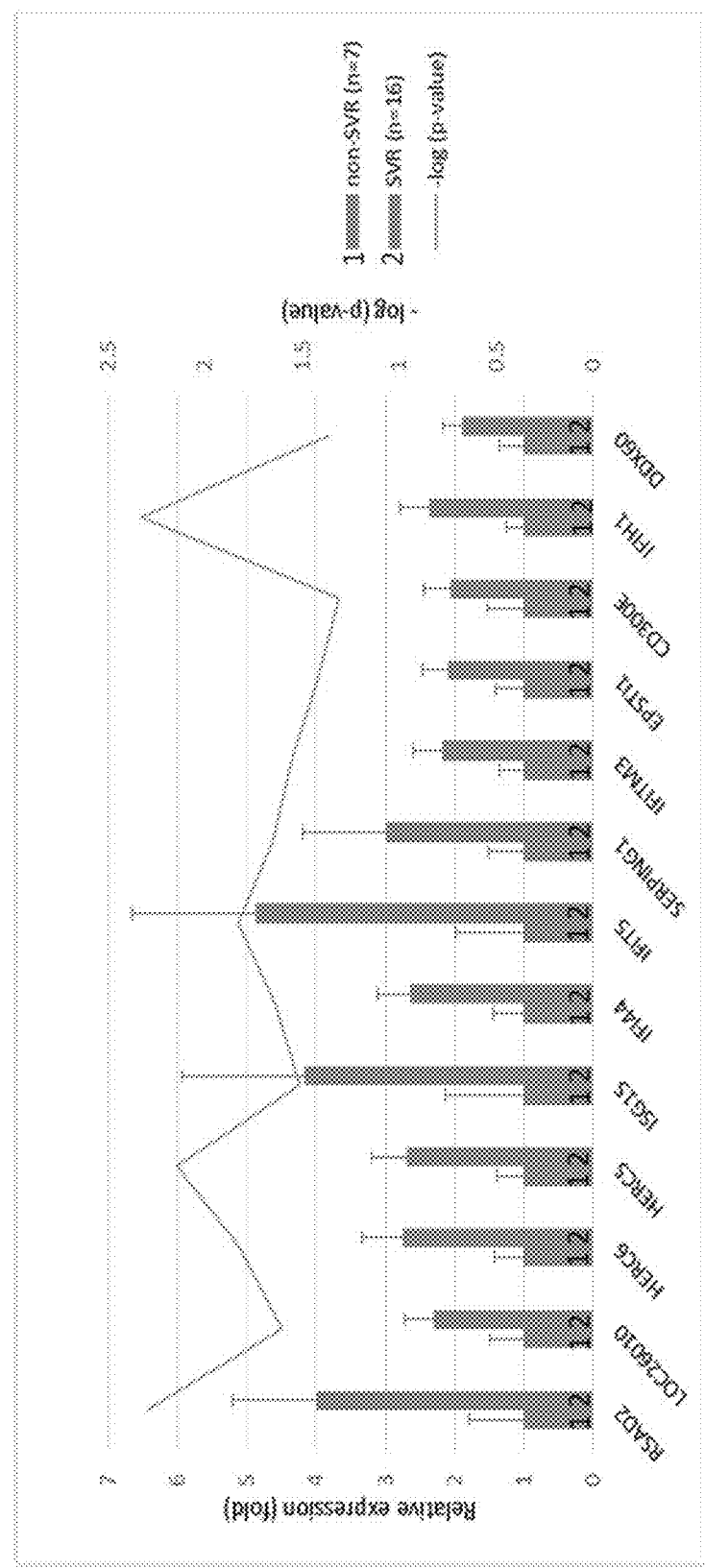
FIG. 1 shows the differentially expressed genes between SVR and non-SVR at week 1. The genes validated by real-time PCR with p-value <0.05 are listed. The bar presents mean of fold change±SE. The relative expression of fold change is normalized by endogenous GADPH.

This invention is aimed to establish a genetic model to predict the treatment response for HCV genotype 1 infected patients undergoing peginterferon plus ribavirin therapy. By exploring the dynamic PBMC gene expression profile during pegIFN plus ribavirin therapy, we identified the target genes related with treatment efficacy for HCV patients. We select 8 target genes (RSAD2, LOC26010, HERC5, HERC6, IFI44, SERPING1, IFITM3, and DDX60) at week 1 as the major components of a scoring method to predict the treatment outcome of HCV patients. This predictive model can reliably identify the responders and non-responders after one week of peginterferon plus ribavirin therapy (area under the ROC curve (AUC)=0.89, p=0.007 for SVR; AUC=0.95, p=0.003 for cEVR), especially among the patients carrying the favorable IL28B rs8099917 TT genotype (AUC=0.89, p=0.002 for SVR; AUC=1.0, p=0.008 for cEVR). The performance of this predictive model is superior to traditional predictors, such as the RVR, viral load and IL28B rs8099917 genotype. The model will help clinicians adopt an appropriate strategy for chronic HCV genotype 1 patients at an earlier time point.

DETAIL DESCRIPTION OF THE INVENTION

Unless otherwise specified, "a" or "an" means "one or more".

In the present invention, we establish a molecular predictive model for the early stratification of the responders and non-responders to pegIFN plus ribavirin therapy, especially among patients carrying the favorable IL28B rs8099917 TT genotype. The performance of this genetic model is better than the traditional predictors, such as the RVR (rapid virologic response), viral load and IL28B genotype. This model advance the predictive time for SVR (sustained virologic response) by one week of pegIFN plus ribavirin therapy compared with the RVR. It helps clinicians adopt appropriate strategies for HCV genotype 1 infected patients at an earlier time point.

The present invention provides a method for predicting treatment efficacy of peginterferon plus ribavirin treatment in a subject suffering from chronic hepatitis C comprising: (a) measuring gene expression levels of genes comprising RSAD2, LOC26010, HERC5, HERC6, IFI44, SERPING1, IFITM3 and DDX60 of a blood sample from the subject after one week of the peginterferon plus ribavirin treatment; and (b) calculating a gene score according to cumulative fold change of the gene expression levels, when the gene score is equal to or higher than a cut-off value, the method predicts successful treatment of chronic hepatitis C with the peginterferon plus ribavirin treatment for the subject.

In a preferred embodiment of the present invention, wherein the gene score is cumulative fold change of RSAD2, LOC26010, HERC5, HERC6, IFI44, SERPING1, IFITM3 and DDX60 genes. In a more preferred embodiment of the present invention, wherein the cumulative fold change of RSAD2, LOC26010, HERC5, HERC6, IFI44, SERPING1, IFITM3 and DDX60 genes is calculated by the sum of fold change (RSAD2+LOC26010+HERC5+HERC6+IFI44+SERPING1+IFITM3+DDX60), wherein fold change=$2^{-ddCt}$, wherein dCt=Ct (gene X)–Ct (GADPH) and ddCt=dCt–mean dCt (gene X of non-sustained virologic response patients).

In a preferred embodiment of the present invention, wherein the cut-off value is determined by the sum of sensitivity and specificity achieving its maximal on a ROC (receiver operating characteristic) curve. In a more preferred embodiment of the present invention, wherein the cut-off value is 8.

In a preferred embodiment of the present invention, the subject is a patient infected with HCV genotype 1.

Based on the present invention, the blood sample comprises peripheral blood mononuclear cells.

In a preferred embodiment of the present invention, it is reliably identified HCV genotype 1 patients with an expected null response to pegIFN/ribavirin therapy using a cut-off value of less than 8. In the overall cases, the sensitivity, specificity, positive predictive value (PPV) and negative predictive value (NPV) for the prediction of both SVR and cEVR are 93.8%, 57.1%, 83.3% and 80.0%, respectively. In subpopulation of IL28B rs8099917 TT genotypes, the sensitivity, specificity, PPV and NPV for SVR prediction are 92.9%, 75.0%, 92.9%, and 75.0%, respectively. Among the patients carrying the IL28B TT genotype, the sensitivity, specificity, PPV and NPV for complete early virologic response (cEVR) prediction are 93.3%, 100%, 100%, and 75.0%, respectively. Using the ROC curve analysis, the predictive performance of this method is superior to the traditional predictors, such as the RVR, viral load and IL28B genotype.

In HCV genotype 1 patients, a 48 week-peginterferon plus standard dose of ribavirin regimen has an SVR rate that ranges from 44%-79%. Less than 1.6% of HCV genotype 1 patients without complete early virologic response (cEVR) have the opportunity to achieve a SVR. Even extending the treatment duration from 48 weeks to 72 weeks, the SVR rate was only 38% for HCV genotype 1 patients with partial early virologic response (pEVR) and 5% for those without cEVR. The current treatment guidelines recommend the HCV genotype 1 patients who fail to achieve an EVR at week 12 should stop pegIFN/ribavirin therapy. The method of the present invention has reliable accuracy to predict SVR and cEVR, especially among patients carrying the IL28B rs8099917 TT genotype. Patients who are predicted to be non-cEVR based on the week 1 score should stop pegIFN/ribavirin therapy and wait for direct-acting antiviral agents (DAAs). Guided by this predictive model, clinicians could tailor individual treatment strategies as soon as possible. This method offers a cost-effective solution for the predicament of HCV therapy and avoids the unnecessary adverse effects of the interferon-based regimen.

EXAMPLES

Subjects

A total of 27 treatment naïve chronic hepatitis C patients were enrolled from Kaohsiung Medical University Hospital. The inclusion criteria were as follows: (a) adults aged more than 18 years with anti-HCV and detectable serum HCV RNA for more than 6 months; (b) infection with HCV genotype 1; and (c) serum ALT (alanine aminotransferase) increased by more than 1.5-fold over the normal range. The exclusion criteria were as follows: coinfection with hepatitis B, hepatitis D or human immunodeficiency virus and the presence of decompensated liver cirrhosis, primary biliary cirrhosis, autoimmune hepatitis, sclerosing cholangitis, al-antitrypsin deficiency, Wilson disease, psychiatric conditions, current or past history of alcohol abuse (≥20 g daily), previous liver transplantation, or the presence of hepatocellular carcinoma or other malignancies. This study was approved by the Kaohsiung Medical University Hospital Institutional Review Board according to the guidelines of the Declaration of Helsinki and the principles of good clinical practice. Written informed consent was obtained from all participants.

Assessment of Treatment Efficacy

All participants were subcutaneously treated with peginterferon α-2a (180 μg/week) plus weight-based ribavirin (1000 mg/day for weights <75 kg and 1200 mg/day for weights ≥75 kg) for 48 weeks. All of the patients achieved an 80/80/80 treatment adherence of 48-week peginterferon/ribavirin, defined as receiving >80% of peginterferon, >80% of ribavirin and >80% of treatment duration. A sustained virologic response (SVR) was defined as undetectable HCV RNA throughout the 24 weeks after the completion of therapy. A complete early virologic response (cEVR) was defined as undetectable HCV RNA at week 12. A partial early virologic response (pEVR) was defined as a more than 2 $\log_{10}$ IU/ml decline in the HCV RNA from baseline at week 12. A rapid virologic response (RVR) was defined as seronegativity for HCV RNA after 4 weeks of therapy. The non-SVR cohort included patients with either relapse or nonresponse.

Cell Preparation and RNA Extraction

Peripheral blood was collected from the study participants at baseline and during the 1st and 4th weeks. Peripheral blood mononuclear cells (PBMCs) were isolated from white blood cells by the standard Ficoll-Hypaque Plus (Amersham Biosciences, Uppsala, Sweden) density gradient separation technique. RNA was purified from the PBMCs using the RIBOPURE™ Kit (Ambion, Applied Biosystems, Foster City, Calif., USA) following the manufacturer's instructions. The RNA integrity was assessed by agarose electrophoresis. RNA samples with an A260:280 ratio >1.8 were selected for the microarray. The isolated RNA was used as the template for one round of reverse transcription to generate cDNA with the ThermoScript RT-PCR System.

Detection of HCV

Hepatitis C virus antibodies (anti-HCV) were detected using a third-generation commercially available enzyme-linked immunosorbent assay kit (Abbott Laboratories, Chicago, Ill., USA). Serum HCV RNA was quantified using a real-time polymerase chain reaction assay (Vermehren J, Yu M L, Monto A, Yao J D, Anderson C, Bertuzis R, Schneider G, Sarrazin C. Multi-center evaluation of the Abbott Real-Time HCV assay for monitoring patients undergoing antiviral therapy for chronic hepatitis C. J Clin Virol. 2011; 52:133-137) (RealTime HCV; Abbott Molecular, Des Plaines Ill., USA; detection limit: 50 IU/ml). HCV genotypes were identified using the method proposed by Okamoto et al. (Okamoto H, Tokita H, Sakamoto M, Horikita M, Kojima M, Iizuka H, Mishiro S. Characterization of the genomic sequence of type V (or 3a) hepatitis C virus isolates and PCR primers for specific detection. J Gen Virol. 1993; 74:2385-2390).

SNP Genotyping

The IL28B rs8099917 genotype was significantly linked with the treatment response to PegIFN/ribavirin therapy by a genome-wide association study and replication studies in Asian cohorts (Tanaka Y, Nishida N, Sugiyama M, Kurosaki M, Matsuura K, Sakamoto N, Nakagawa M, Korenaga M, Hino K, Hige S, Ito Y, Mita E, Tanaka E, et al. Genome-wide association of IL28B with response to pegylated interferon-alpha and ribavirin therapy for chronic hepatitis C. Nat Genet. 2009; 41:1105-1109). The rs80999917 genotypes were identified using the ABI TAQMAN® SNP genotyping assays (Applied Biosystems, CA, USA) with the pre-designed primer and probe (ABI Assay ID: C_11710096_10) in accordance with the manufacturer's recommendations.

Microarray Data Analysis

Complementary RNA was prepared from the total RNA and hybridized to the Affymetrix Human gene 1.0 ST arrays (28869 probe sets) following the manufacturer's protocols (Affymetrix, Santa Clara, Calif., USA). The hybridized arrays were scanned on an AFFYMETRIX GENECHIP®) scanner 3000. The initial quantification of the array images was performed by utilizing the AFFYMETRIX GENECHIP Operating Software (GCOS). Then, the data were analyzed by the R package (Irizarry R A, Hobbs B, Collin F, Beazer-Barclay Y D, Antonellis K J, Scherf U, Speed T P. Exploration, normalization, and summaries of high density oligonucleotide array probe level data. Biostatistics. 2003; 4:249-264), which performed normalization, calculated gene expression levels, and determined the statistical significance. The threshold for significance in expression changes was set at a fold change $\geq 2$ and false discovery rate (FDR)<0.05 using the Benjamini-Hochberg procedure (Benjamini Y, Hochberg Y. Controlling the false discovery rate: a practical and powerful approach to multiple testing. Journal of the Royal Statistical Society, Series B. 1995; 57:289-300).

Quantitative Polymerase Chain Reaction

Differentially expressed genes obtained from the microarray data were validated by quantitative PCR. mRNA samples were used for cDNA synthesis and processed using TAQMAN Gene Expression Assays (Applied Biosystems). Primer and probe sets purchased from Life Technologies were pre-designed for the respective genes. The reaction was executed by applying the TAQMAN® Gene Expression Master Mix (Applied Biosystems) on a 7500 Real-Time PCR System (Applied Biosystems). The standard thermal condition was 10 minutes at 95° C. for polymerase activation, followed by 40 cycles of 95° C. for 15 seconds and 60° C. for 60 seconds. The expression of candidate genes was normalized to the endogenous GADPH. Relative gene expression was calculated using the $\Delta\Delta Ct$ method.

Statistical Analysis

Student's t test was performed to analyze continuous variables. The Chi-square ($X^2$) test or Fisher's exact test was used to assess categorical variables. The area under the curve (AUC) was calculated using receiver-operating characteristics (ROC) analysis and used to assess the capability of the predictive models. The optimum cut-off value to divide the risk strata was calculated by the Yauden index. The significance of AUC values between two predictive models was compared by the Hanley and McNeil method (Hanley J A, McNeil B J. A method of comparing the areas under receiver operating characteristic curves derived from the same cases. Radiology. 1983; 148:839-843). A two-tailed p-value <0.05 was considered statistically significant. All of the statistical analyses were performed using the Statistic Packages for Social Science Program (SPSS version 13.0 for windows, SPSS Inc., Chicago, Ill., USA).

Baseline Characteristics

The demographic characteristics of the study subjects are shown in Table 1. A total of 27 HCV genotype 1 patients (screening dataset n=7; validation dataset n=20) treated with 48 weeks of pegIFN/ribavirin were recruited in this study. Four (57.1%) patients in the screening study and 12 (60.0%) patients in the validation study achieved a sustained virologic response (SVR). The frequency of the favorable IL28B rs8099917 TT genotype in the overall cases was 83.3%. All patients carrying the unfavorable IL28B rs8099917 GT genotype (n=4) failed to achieve SVR. There was no significant difference in the gender, age, GOT, GPT, viral load and IL28B rs8099917 genotype in the screening and validation datasets. The baseline demographic characteristics were comparable between the screening and validation datasets.

TABLE 1

Baseline demographics of HCV genotype 1 patients

| | Screening | | | Validation | | | Screening vs. Validation p-value | |
|---|---|---|---|---|---|---|---|---|
| | SVR | non-SVR | p-value | SVR | non-SVR | p-value | SVR | non-SVR |
| n | 4 | 3 | | 12 | 8 | | — | — |
| Age (years, mean ± SD) | 49.0 ± 17.6 | 49.7 ± 8.6 | 0.955 | 42.4 ± 10.6 | 42.8 ± 12.8 | 0.950 | 0.516 | 0.416 |
| Sex (M/F) | 4/0 | 2/1 | 0.429 | 8/4 | 7/1 | 0.603 | 0.376 | 0.491 |

TABLE 1-continued

Baseline demographics of HCV genotype 1 patients

| | Screening | | | Validation | | | Screening vs. Validation p-value | |
|---|---|---|---|---|---|---|---|---|
| | SVR | non-SVR | p-value | SVR | non-SVR | p-value | SVR | non-SVR |
| GOT (IU/L, mean ± SD) | 144.8 ± 178.2 | 127.0 ± 36.5 | 0.875 | 68.0 ± 36.8 | 62.1 ± 48.5 | 0.762 | 0.454 | 0.067 |
| GPT (IU/L, mean ± SD) | 74.5 ± 25.2 | 171.7 ± 92.8 | 0.207 | 120.4 ± 86.1 | 97.8 ± 67.2 | 0.539 | 0.320 | 0.172 |
| HCV RNA (log IU/ml) | 5.33 ± 1.34 | 6.44 ± 0.75 | 0.259 | 5.03 ± 1.02 | 5.69 ± 0.90 | 0.154 | 0.218 | 0.147 |
| IL28B rs8099917 TT | 4 (100.0%) | 2 (66.7%) | 0.429 | 10 (100.0%) | 4 (57.1%) | 0.051 | — | 1.000 |
| IL28B rs8099917 GT | 0 (0.0%) | 1 (33.3%) | | 0 (0.0%) | 3 (42.9%) | | | |

Microarray Analysis

Forty-three differentially expressed genes were obtained from the microarray profiling of the PBMC samples (SVR n=4; non-SVR n=3) during pegIFN/ribavirin therapy. Among the 43 differentially expressed genes, 16 genes at week 1 and 23 genes at week 4 were significantly upregulated in the SVR group compared with the non-SVR group. In contrast, four genes at week 4 were significantly downregulated in the SVR group compared with the non-SVR group. A total of 43 genes were candidates for real-time PCR validation.

Real-Time PCR Validation

Figure 2:
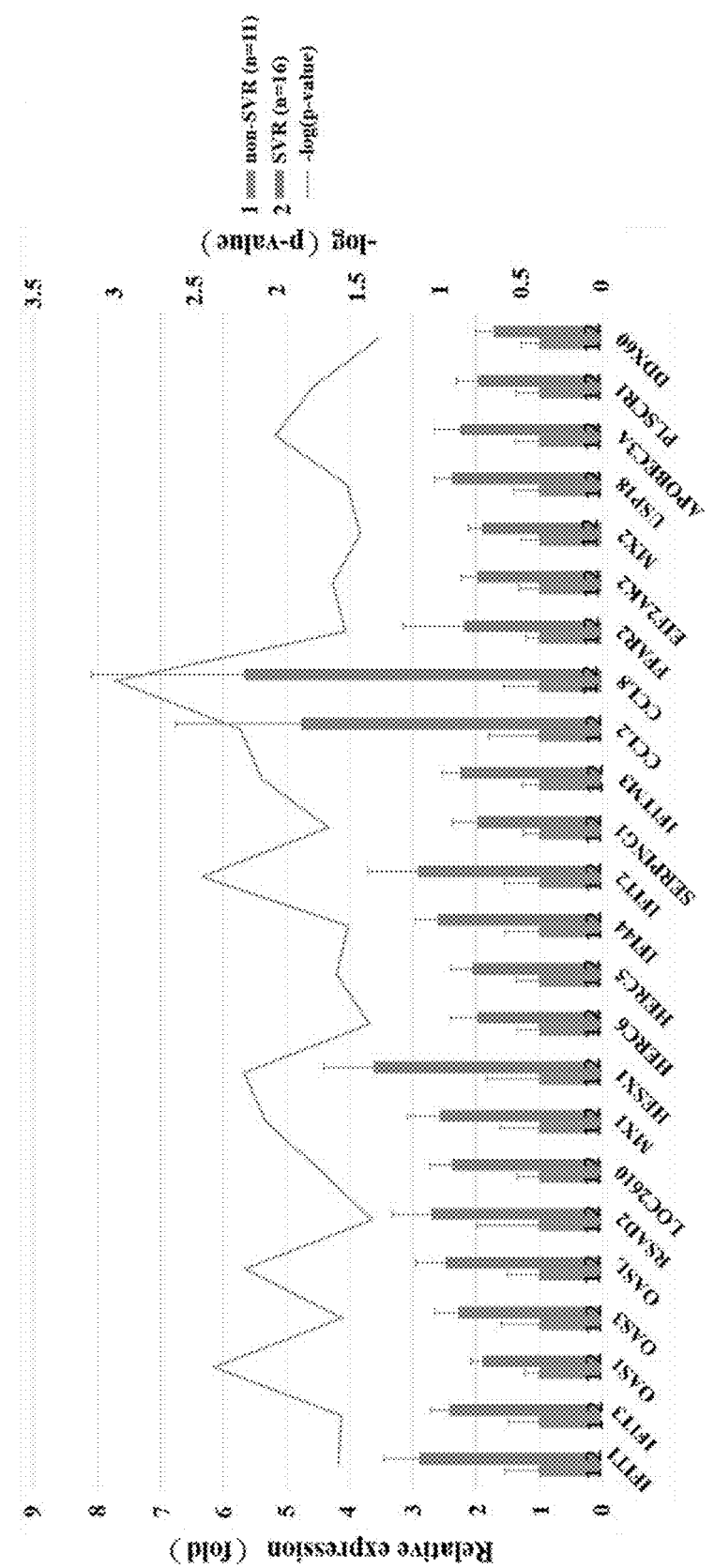
FIG. 2 shows the differentially expressed genes between SVR and non-SVR at week 4. The genes validated by real-time PCR with p-value <0.05 are listed. The bar presents mean of fold change±SE. The relative expression of fold change is normalized by endogenous GADPH.

The PBMC gene expression signature at baseline was not significantly different between the responders and non-responders. Thirteen genes at week 1 (FIG. 1) and 24 genes at week 4 (FIG. 2) were significantly upregulated in the SVR group compared with the non-SVR group. Twenty-five genes at week 1 and 27 genes at week 4 were significantly upregulated in the cEVR group compared to the non-cEVR group. None of the significantly downregulated genes at baseline, week 1 and week 4 were confirmed by quantitative PCR.

The Development of the Genetic Predictive Model

We attempted to establish a genetic model to predict the treatment outcome of pegIFN plus ribavirin for HCV patients. We speculated that the genes correlated with the treatment response are persistently expressed during pegIFN plus ribavirin therapy. The target genes of the predictive model met the following criteria: (1) the differentially expressed genes between the SVR and non-SVR groups (fold change >1.7 and p-value <0.05) were present at both weeks 1 and 4. (2) The minimal number of target genes was favored under the premise of the precise prediction of the treatment outcome. We selected 8 target genes (RSAD2, LOC26010, HERC5, HERC6, IFI44, SERPING1, IFITM3, and DDX60) expressed at both weeks 1 and 4 as the major components of the predictive model. The cellular locations and functions of these target genes were listed in Table 2. The gene score was defined as the cumulative fold change of the candidate genes [i.e., gene score=sum of fold change (RSAD2+LOC26010+HERC5+HERC6+IFI44+SERPING1+IFITM3+DDX60), wherein fold change=$2^{-ddCt}$, wherein dCt=Ct (gene X)−Ct (GADPH) and ddCt=dCt−mean dCt (gene X of non-sustained virologic response patients)]. The expression of the candidate genes was normalized to the GADPH endogenous control. The relative expression of the candidate genes was compared with the mean dCt of the non-SVR group.

TABLE 2

List of gene panel

| Symbol | Chr. | Location | Gene name | Function |
|---|---|---|---|---|
| LOC26010 | 2q33.1 | Nucleus | viral DNA polymerase-transactivated protein 6 | Involved in ribosome biogenesis and translational control in response to oxidative stress. |
| IFI44 | 1p31.1 | Cytoplasm | interferon-induced protein 44 | This protein aggregates to form microtubular structures |
| RSAD2 | 2p25.2 | Cytoplasm | radical S-adenosyl methionine domain containing 2 | Involved in antiviral defense. May impair virus budding by disrupting lipid rafts at the plasma membrane. |

TABLE 2-continued

List of gene panel

| Symbol | Chr. | Location | Gene name | Function |
|---|---|---|---|---|
| HERC5 | 4q22.1 | Cytoplasm | hect domain and RLD 5 | Major E3 ligase for ISG15 conjugation. |
| HERC6 | 4q22.1 | Cytoplasm | hect domain and RLD 6 | E3 ubiquitin-protein ligase |
| DDX60 | 4q32.3 | Cytoplasm | DEAD (Asp-Glu-Ala-Asp) box polypeptide 60 | ATP and RNA binding |
| IFITM3 | 11p15.5 | Plasma Membrane | interferon induced transmembrane protein 3 (1-8U) | IFN-induced antiviral protein that mediates cellular innate immunity by inhibiting the early steps of replication. |
| SERPING1 | 11q12-q13.1 | Extracellular Space | serpin peptidase inhibitor, clade G (C1 inhibitor), member 1, (angioedema, hereditary) | Activation of the C1 complex is under control of the C1-inhibitor. |

The Performance of the Genetic Predictive Model

Overall Study Population

To evaluate the association between this scoring method and the pegIFN plus ribavirin treatment response, we divided the subjects into high and low gene score groups. By performing a ROC analysis, we established a cut-off value of 8 for the gene score at week 1. Patients with a high gene score (≥8) had significantly greater SVR rates than those with a low gene score (<8) (83.3% vs. 20.0%, OR=4.8, 95% C.I=1.56-14.74, p=0.017). Similarly, the patients with low gene scores had significantly higher risk of failing to achieve cEVR compared with those with high gene scores (80.0% vs. 16.7%, OR=4.8, 95% C.I=1.56-14.74, p=0.017) (Table 3).

TABLE 3

The association between gene score and pegIFN plus ribavirin treatment response in overall cases

| Score (W1) | SVR | non-SVR | Fisher's p-value | OR (95% C.I) | cEVR | non-cEVR | Fisher's p-value | OR (95% C.I) |
|---|---|---|---|---|---|---|---|---|
| ≥8 | 15 (83.3%) | 3 (16.7%) | 0.017 | 4.8 (1.56~14.74) | 15 (83.3%) | 3 (16.7%) | 0.017 | 4.8 (1.56~14.74) |
| <8 | 1 (20.0%) | 4 (80.0%) | | | 1 (20.0%) | 4 (80.0%) | | |

Gene score = the sum of fold change (RSAD2 + LOC26010 + HERC5 + HERC6 + IFI44 + SERPING1 + IFITM3 + DDX60).

Figure 3A:
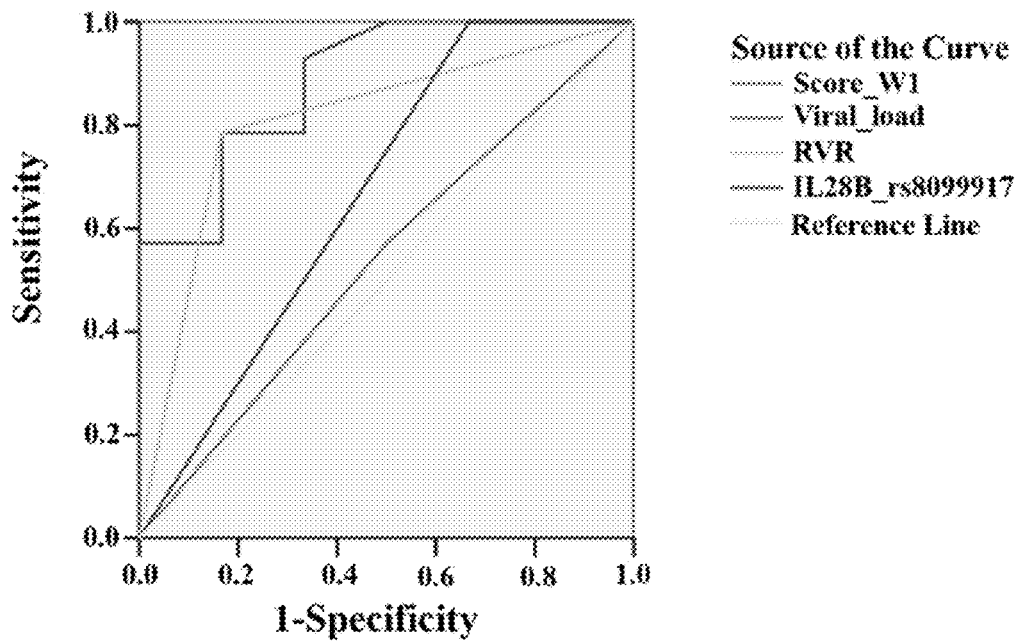
FIG. 3a shows the comparisons of predictors for sustained virologic response (SVR) in overall cases.
Figure 3B:
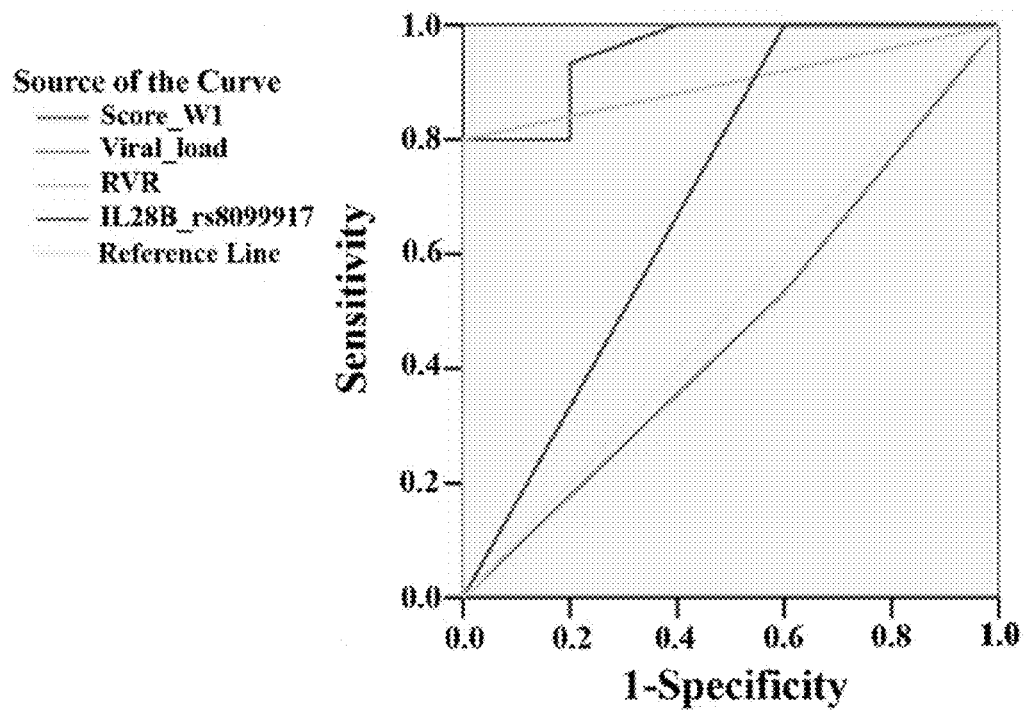
FIG. 3b shows the comparisons of predictors for complete early virologic response (cEVR) in overall cases.

The important predictors for pegIFN plus ribavirin therapy treatment outcomes include the RVR, viral load and IL28B genotype. RVR is well-known as the single best predictor for SVR (Yu M L, Dai C Y, Huang J F, Chiu C F, Yang Y H, Hou N J, Lee L P, Hsieh M Y, Lin Z Y, Chen S C, Hsieh M Y, Wang L Y, Chang W Y, et al. Rapid virological response and treatment duration for chronic hepatitis C genotype 1 patients: a randomized trial. Hepatology. 2008; 47:1884-1893). We compared the predictive performance among this scoring method and the traditional predictors in the overall cases by calculating the area under the ROC curve (AUC). The AUC of week 1 gene score (AUC=0.89, p=0.0074) was substantially higher than that of RVR (AUC=0.81, p=0.032) for the prediction of SVR (FIG. 3a). The AUC value of week 1 gene score for the prediction of cEVR (AUC=0.95, p=0.003) was also substantially higher than that of RVR (AUC=0.90, p=0.0088) (FIG. 3b). However, both of the differences did not reach statistical significance. (RVR vs. gene score: p=0.2998 for SVR; p=0.4384 for cEVR) (Table 4).

TABLE 4

The area under the ROC curve in overall cases

| | SVR | | | | cEVR | | | |
|---|---|---|---|---|---|---|---|---|
| Variable | AUC | 95% C.I | p-value | Predictor vs. gene score p-value | AUC | 95% C.I | p-value | Predictor vs. gene score p-value |
| Gene score (W1) | 0.89 | (0.73~1.04) | 0.0074 | Reference | 0.95 | (0.86~1.05) | 0.0030 | Reference |
| Viral load | 0.54 | (0.25~0.82) | 0.8046 | 0.0525 | 0.47 | (0.17~0.76) | 0.8273 | 0.0013 |
| RVR | 0.81 | (0.59~1.03) | 0.0320 | 0.2998 | 0.90 | (0.76~1.04) | 0.0088 | 0.4384 |
| IL28B rs8099917 | 0.67 | (0.38~0.96) | 0.2482 | 0.1072 | 0.70 | (0.39~1.01) | 0.1904 | 0.1032 |

AUC: area under the ROC curve

Subpopulation with IL28B TT Genotypes

Because the IL28B rs8099917 TT genotype was a favorable predictor for SVR, we stratified the study population in terms of the IL28B genotypes. We analyzed the association of the week 1 gene score and treatment response among the IL28B TT subpopulation. The SVR rate was significantly elevated in the high week 1 score group compared with the low week 1 score group in patients carrying the TT genotype (92.9% vs. 25.0%, OR=10.5, 95% C.I=1.46-75.4, p=0.019). Furthermore, the patients with a high week 1 score had a significantly greater cEVR rate compared with those with a low week 1 score among the IL28B TT subpopulation (100% vs. 25%, p=0.005) (Table 5).

TABLE 5

The association between gene score and pegIFN plus ribavirin treatment response in IL28B rs80999917 TT genotype

| Score (W1) | SVR | non-SVR | Fisher's p-value | OR (95% C.I) | cEVR | non-cEVR | Fisher's p-value | OR (95% C.I) |
|---|---|---|---|---|---|---|---|---|
| ≥8 | 13 (92.9%) | 1 (7.1%) | 0.019 | 10.5 (1.46~75.4) | 14 (100.0%) | 0 (0.0%) | 0.005 | — |
| <8 | 1 (25.0%) | 3 (75.0%) | | | 1 (25.0%) | 3 (75.0%) | | | gene score = the sum of fold change (RSAD2 + LOC26010 + HERC5 + HERC6 + IFI44 + SERPING1 + IFITM3 + DDX60).

Figure 4A:
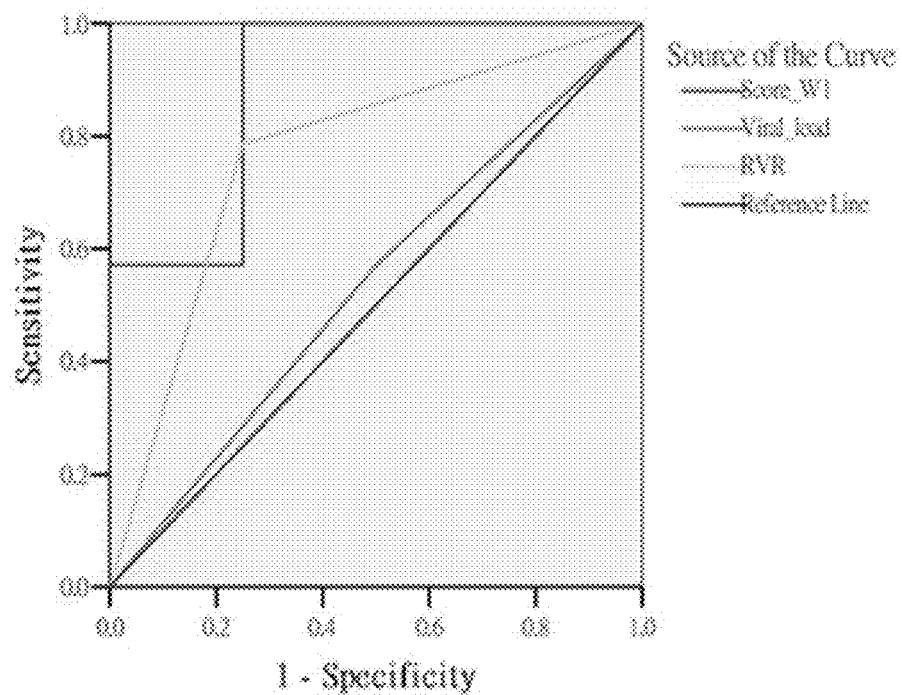
FIG. 4a shows the comparisons of predictors for SVR in subjects carrying IL-28B rs8099917 TT genotype.
Figure 4B:
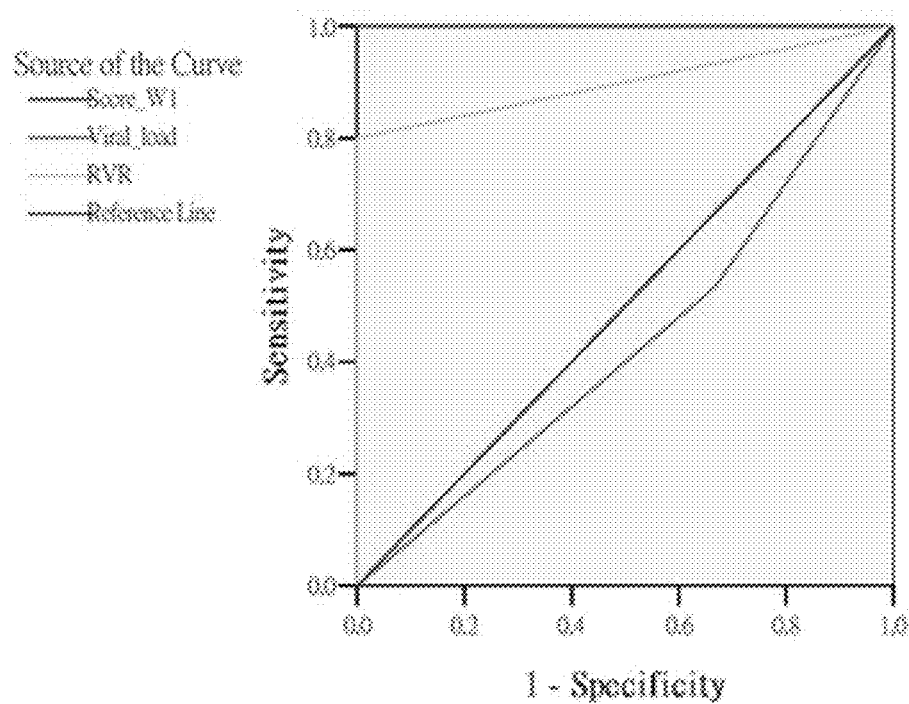
FIG. 4b shows the comparisons of predictors for cEVR in subjects carrying IL-28B rs8099917 TT genotype.

We evaluated the predictive performance between this scoring method and other predictors among the patients carrying the IL28B TT genotype (Table 6). The AUC value of week 1 gene score (AUC=0.89, p=0.0195) to predict SVR was significantly higher than that of RVR (AUC=0.77, p=0.1112) (RVR vs. gene score: p=0.0413) (FIG. 4a). The week 1 gene score had an excellent predictive performance for cEVR (AUC=1.00, p=0.0077) that was superior to the RVR with borderline significance (AUC=0.90, p=0.0330) (RVR vs. gene score: p=0.0614) (FIG. 4b).

TABLE 6

The area under the ROC curve in subjects with IL28B rs8099917 TT genotype

| | SVR | | | | cEVR | | | |
|---|---|---|---|---|---|---|---|---|
| Variable | AUC | 95% C.I | p-value | Predictor vs. gene score p-value | AUC | 95% C.I | p-value | Predictor vs. gene score p-value |
| Gene score (W1) | 0.89 | (0.69~1.09) | 0.0195 | Reference | 1.00 | (1.00~1.00) | 0.0077 | Reference |
| Viral load | 0.54 | (0.21~0.87) | 0.8318 | 0.1294 | 0.43 | (0.08~0.79) | 0.7223 | 0.0158 |
| RVR | 0.77 | (0.49~1.05) | 0.1112 | 0.0413 | 0.90 | (0.75~1.05) | 0.0330 | 0.0614 |

AUC: area under the ROC curve

What is claimed is:

1. A method for predicting treatment efficacy of peginterferon plus ribavirin treatment in a subject suffering from chronic hepatitis C genotype 1 comprising:
   (a) measuring gene expression levels of genes comprising RSAD2, LOC26010, HERC5, HERC6, IFI44, SERPING1, IFITM3 and DDX60 of a blood sample from the subject after receiving one week of the peginterferon plus ribavirin treatment;
   (b) calculating a gene score according to cumulative fold change of the gene expression levels; and
   (c) comparing the gene score to a cut-off value, wherein the cut-off value is determined by the sum of sensitivity and specificity achieving its maximal on a ROC (receiver operating characteristic) curve, wherein when the gene score is equal to or higher than the cut-off value, it is indicative that the subject is responsive to the peginterferon plus ribavirin treatment.

2. The method of claim 1, wherein the gene score is cumulative fold change of RSAD2, LOC26010, HERC5, HERC6, IFI44, SERPING1, IFITM3 and DDX60 genes.

3. The method of claim 2, wherein the cumulative fold change of RSAD2, LOC26010, HERC5, HERC6, IFI44, SERPING1, IFITM3 and DDX60 genes is calculated by sum of fold change (RSAD2+LOC26010+HERC5+HERC6+IFI44+SERPING1+IFITM3+DDX60), wherein fold change=2-acct, wherein dCt=Ct (gene X)−Ct (GADPH) and ddCt=dCt−mean dCt (gene X of non-sustained virologic response patients).

4. The method of claim 1, wherein the cut-off value is 8.

5. The method of claim 1, wherein the blood sample comprises peripheral blood mononuclear cells.

* * * * *